United States Patent
Takagi et al.

(10) Patent No.: US 11,712,158 B2
(45) Date of Patent: Aug. 1, 2023

(54) OPTICAL FIBER BUNDLE MANUFACTURING APPARATUS, LIGHT GUIDE, ENDOSCOPE HAVING LIGHT GUIDE, AND METHOD OF MANUFACTURING OPTICAL FIBER BUNDLE

(71) Applicant: OLYMPUS CORPORATION, Tokyo (JP)

(72) Inventors: Hiroki Takagi, Shiki (JP); Ken Tamura, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 135 days.

(21) Appl. No.: 17/131,915

(22) Filed: Dec. 23, 2020

(65) Prior Publication Data
US 2021/0109282 A1    Apr. 15, 2021

Related U.S. Application Data

(63) Continuation of application No. PCT/JP2019/006137, filed on Feb. 19, 2019.

(30) Foreign Application Priority Data

Jul. 4, 2018    (JP) .................................. 2018-127778

(51) Int. Cl.
| | | |
|---|---|---|
| *A61B 1/06* | (2006.01) | |
| *A61B 1/00* | (2006.01) | |

(Continued)

(52) U.S. Cl.
CPC .......... *A61B 1/0669* (2013.01); *A61B 1/0011* (2013.01); *A61B 1/000095* (2022.02);
(Continued)

(58) Field of Classification Search
None
See application file for complete search history.

(56) References Cited

U.S. PATENT DOCUMENTS

| 5,204,927 A | 4/1993 | Chin et al. | |
|---|---|---|---|
| 5,376,201 A * | 12/1994 | Kingstone | G02B 6/04 385/116 |

(Continued)

FOREIGN PATENT DOCUMENTS

| CN | 104238007 A | 12/2014 |
|---|---|---|
| JP | S46-018784 B1 | 5/1971 |

(Continued)

OTHER PUBLICATIONS

International Search Report dated Apr. 23, 2019 issued in PCT/JP2019/006137.

*Primary Examiner* — Michelle R Connelly
(74) *Attorney, Agent, or Firm* — Scully, Scott, Murphy & Presser, P.C.

(57) ABSTRACT

An optical fiber bundle manufacturing apparatus includes: a winding member; a guide member movable in a direction parallel to a rotary axis, the guide member being configured to guide an optical fiber wire to any one of first winding positions, a converging winding position and second winding positions; and a processor configured to perform processing to move the guide member such that a first branching portion branching into p branches, a converging portion converging the first branching portion branching into p branches into one, a second branching portion branching into q branches, and a connecting portion connecting the first branching portion and the second branching portion are formed in this order by the optical fiber wire.

16 Claims, 17 Drawing Sheets

(51) Int. Cl.
*A61B 1/07* (2006.01)
*G02B 6/04* (2006.01)
*G02B 6/44* (2006.01)
*C03B 37/00* (2006.01)

(52) U.S. Cl.
CPC ............ *A61B 1/00167* (2013.01); *A61B 1/07* (2013.01); *G02B 6/04* (2013.01); *G02B 6/4403* (2013.01); *A61B 1/0655* (2022.02); *A61B 1/0661* (2013.01); *C03B 37/00* (2013.01)

(56) References Cited

U.S. PATENT DOCUMENTS

| | | | | |
|---|---|---|---|---|
| 6,885,800 | B2* | 4/2005 | Sun | G02B 6/3612 385/54 |
| 7,548,676 | B2* | 6/2009 | Kerr | B29C 43/222 385/115 |
| 10,379,311 | B1* | 8/2019 | Krywicki | G02B 6/3676 |
| 2006/0088258 | A1* | 4/2006 | Sasaki | G02B 6/4403 385/14 |
| 2010/0195955 | A1* | 8/2010 | Burnham | G02B 6/3897 385/24 |

FOREIGN PATENT DOCUMENTS

| | | | |
|---|---|---|---|
| JP | S50-001752 A | | 1/1975 |
| JP | S50-001753 A | | 1/1975 |
| JP | 63092904 A | * | 4/1988 |
| JP | S63-092904 A | | 4/1988 |
| JP | H03-109515 A | | 5/1991 |
| JP | H04-049164 A | | 4/1992 |
| JP | H06-148441 A | | 5/1994 |
| JP | H08-129107 A | | 5/1996 |
| JP | 2683527 B2 | * | 12/1997 |
| JP | 2005-181867 A | | 7/2005 |
| JP | 2005181867 A | * | 7/2005 |
| JP | 2005-208153 A | | 8/2005 |
| JP | 2007-219536 A | | 8/2007 |
| JP | 4091534 B2 | | 5/2008 |
| JP | 4091552 B2 | | 5/2008 |
| JP | 4182362 B2 | | 11/2008 |
| JP | 2009109688 A | * | 5/2009 |
| JP | 2013-198547 A | | 10/2013 |
| JP | 2015-212688 A | | 11/2015 |
| JP | 5816776 B1 | | 11/2015 |
| WO | WO 2013/140961 A1 | | 9/2013 |

* cited by examiner

FIG. 13

| | | \\ CIRCUMFERENTIAL DIRECTION POSITION Y — T3 | | | |
|---|---|---|---|---|---|
| | | Y0 | Y4 | Y7 | Y10 |
| NUMBER OF ROTATIONS Z | Z1 | G | B | C | G |
| | Z2 | G | B | B | G |
| | Z3 | G | B | A | F |
| | Z4 | F | B | C | F |
| | Z5 | F | B | B | F |
| | Z6 | F | B | A | E |
| | Z7 | E | B | C | E |
| | Z8 | E | B | B | E |
| | Z9 | E | B | A | D |
| | Z10 | D | B | C | D |
| | Z11 | D | B | B | D |
| | Z12 | D | B | A | G |

| | | CIRCUMFERENTIAL DIRECTION POSITION Y — T4 | | | |
|---|---|---|---|---|---|
| | | Y0 | Y4 | Y7 | Y10 |
| NUMBER OF ROTATIONS Z | Z1 | I | G | C | I |
| | Z2 | I | G | B | H |
| | Z3 | H | G | C | H |
| | Z4 | H | G | B | G ← X |
| | Z5 | G | G | C | G |
| | Z6 | G | G | B | F |
| | Z7 | F | G | C | F |
| | Z8 | F | G | B | E |
| | Z9 | E | G | C | E |
| | Z10 | E | G | B | I |

OPTICAL FIBER BUNDLE MANUFACTURING APPARATUS, LIGHT GUIDE, ENDOSCOPE HAVING LIGHT GUIDE, AND METHOD OF MANUFACTURING OPTICAL FIBER BUNDLE

CROSS REFERENCE TO RELATED APPLICATION

This application is a continuation application of PCT/JP2019/006137 filed on Feb. 19, 2019 and claims benefit of Japanese Application No. 2018-127778 filed in Japan on Jul. 4, 2018, the entire contents of which are incorporated herein by this reference.

BACKGROUND OF THE INVENTION

1. Field of the Invention

The present invention relates to an optical fiber bundle manufacturing apparatus, a light guide, an endoscope having a light guide, and a method of manufacturing an optical fiber bundle.

2. Description of the Related Art

Conventionally, there has been known a technique where an optical fiber wire is wound around a winding member, and the optical fiber wire on the winding member is collectively cut in a direction orthogonal to a winding direction to manufacture an optical fiber bundle formed of a plurality of optical fiber wires.

For example, Japanese Patent Application Laid-Open Publication No. 6-148441 discloses a method of manufacturing an optical fiber bundle. In the method, a winding position of an optical fiber wire on a circumference of a winding member is moved in a reciprocating manner in a direction orthogonal to a winding direction, at least one of a reciprocating movement speed and a reciprocating movement width is changed irregularly, and the optical fiber wire on the circumference of the winding member is collectively cut in a direction orthogonal to the winding direction to manufacture an optical fiber bundle.

There may be a case where the optical fiber bundle is used as a part of a light guide. For example, in an image pickup apparatus for endoscope or the like, the light guide is, for illuminating an object from a distal end member of an insertion section, disposed between a light source device and the distal end member, and guides illumination light.

There may be a case where an endoscope illuminates an object by illumination light obtained by multiplexing lights of a plurality of light sources. Further, with respect to an illumination light emitting unit which radiates illumination light of an endoscope, there may be a case where a plurality of illumination light emitting units are disposed on a distal end member in conformity with an observation part or an observation purpose.

SUMMARY OF THE INVENTION

According to an aspect of the present invention, there is provided an optical fiber bundle manufacturing apparatus including: a winding member rotatable in a winding direction about a rotary axis and configured to wind up an optical fiber wire; a guide member movable in a direction parallel to the rotary axis, the guide member being configured to guide the optical fiber wire to any one of p first winding positions, a converging winding position, and q second winding positions on an outer peripheral surface of the winding member, where p is a natural number of 2 or more and q is a natural number of 2 or more; and a processor configured to perform processing to move the guide member such that a first branching portion branching into p branches at the first winding positions, a converging portion converging the first branching portion branching into p branches into one at the converging winding position, the second branching portion branching into q branches from the converging portion converging into one at the second winding positions, and a connecting portion connecting the first branching portion and the second branching portion are formed in this order by the optical fiber wire.

According to another aspect of the present invention, there is provided a light guide manufactured by an optical fiber bundle manufacturing apparatus, the optical fiber bundle manufacturing apparatus including: a winding member rotatable in a winding direction about a rotary axis and configured to wind up an optical fiber wire; a guide member movable in a direction parallel to the rotary axis, the guide member being configured to guide the optical fiber wire to any one of p first winding positions, a converging winding position, and q second winding positions on an outer peripheral surface of the winding member, where p is a natural number of 2 or more and q is a natural number of 2 or more; and a processor configured to perform processing to move the guide member such that a first branching portion branching into p branches at the first winding positions, a converging portion converging the first branching portion branching into p branches into one at the converging winding position, the second branching portion branching into q branches from the converging portion converging into one at the second winding positions, and a connecting portion connecting the first branching portion and the second branching portion are formed in this order by the optical fiber wire, wherein a distal end side of the light guide is branched in plurality, and a proximal end side of the light guide is branched in plurality.

According to still another aspect of the present invention, there is provided an endoscope including a light guide manufactured by an optical fiber bundle manufacturing apparatus, the optical fiber bundle manufacturing apparatus including: a winding member rotatable in a winding direction about a rotary axis and configured to wind up an optical fiber wire; a guide member movable in a direction parallel to the rotary axis, the guide member being configured to guide the optical fiber wire to any one of p first winding positions, a converging winding position, and q second winding positions on an outer peripheral surface of the winding member, where p is a natural number of 2 or more and q is a natural number of 2 or more; and a processor configured to perform processing to move the guide member such that a first branching portion branching into p branches at the first winding positions, a converging portion converging the first branching portion branching into p branches into one at the converging winding position, the second branching portion branching into q branches from the converging portion converging into one at the second winding positions, and a connecting portion connecting the first branching portion and the second branching portion are formed in this order by the optical fiber wire, wherein a distal end side of the light guide is branched in plurality, and a proximal end side of the light guide is branched in plurality, and the light guide is configured to guide illumination light from a plurality of light sources to a plurality of illumination light emitting units provided to a distal end member of an insertion section.

According to still another aspect of the present invention, there is provided a method of manufacturing an optical fiber bundle, the method including: preparing a winding member rotatable in a winding direction about a rotary axis and configured to wind up an optical fiber wire, and a guide member movable in a direction parallel to the rotary axis and configured to guide the optical fiber wire to a winding position of the winding member on an outer peripheral surface of the winding member; and performing winding control processing where the winding member is rotated, and the optical fiber wire is wound up while moving the guide member such that an arrangement number of portions of the optical fiber wire on each of paths between p first winding positions on the winding member and q second winding positions on the winding member, which differ from the first winding positions in the circumferential direction position, is arbitrarily set in a distributed manner, where p is a natural number of 2 or more and q is a natural number of 2 or more, and the portions of the optical fiber are converged into one at a position which differs from the first winding position and the second winding position in a circumferential direction and between the first winding position and the second winding position.

BRIEF DESCRIPTION OF THE DRAWINGS

FIG. 13 is a view showing one example of a winding position table of a controller of an optical fiber bundle manufacturing apparatus according to a modification 3 of the embodiment of the present invention;

FIG. 16 is a view showing one example of a winding position table of a controller of an optical fiber bundle manufacturing apparatus according to a modification 4 of the embodiment of the present invention;

DETAILED DESCRIPTION OF THE PREFERRED EMBODIMENT

Hereinafter, an embodiment of the present invention is described with reference to drawings.

Configuration of Embodiment

Figure 1:
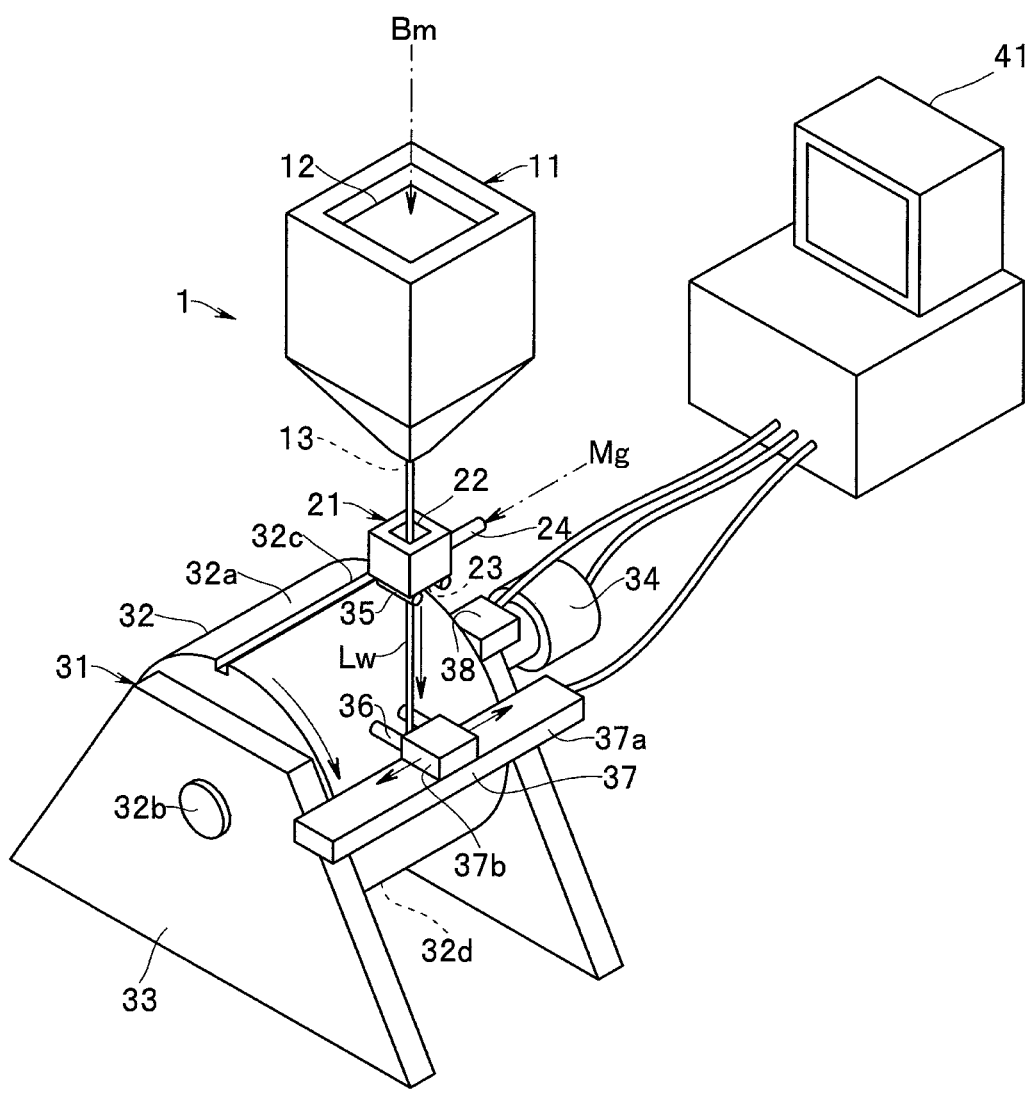
FIG. 1 is a view showing one example of a configuration of an optical fiber bundle manufacturing apparatus according to an embodiment of the present invention.
Figure 2:
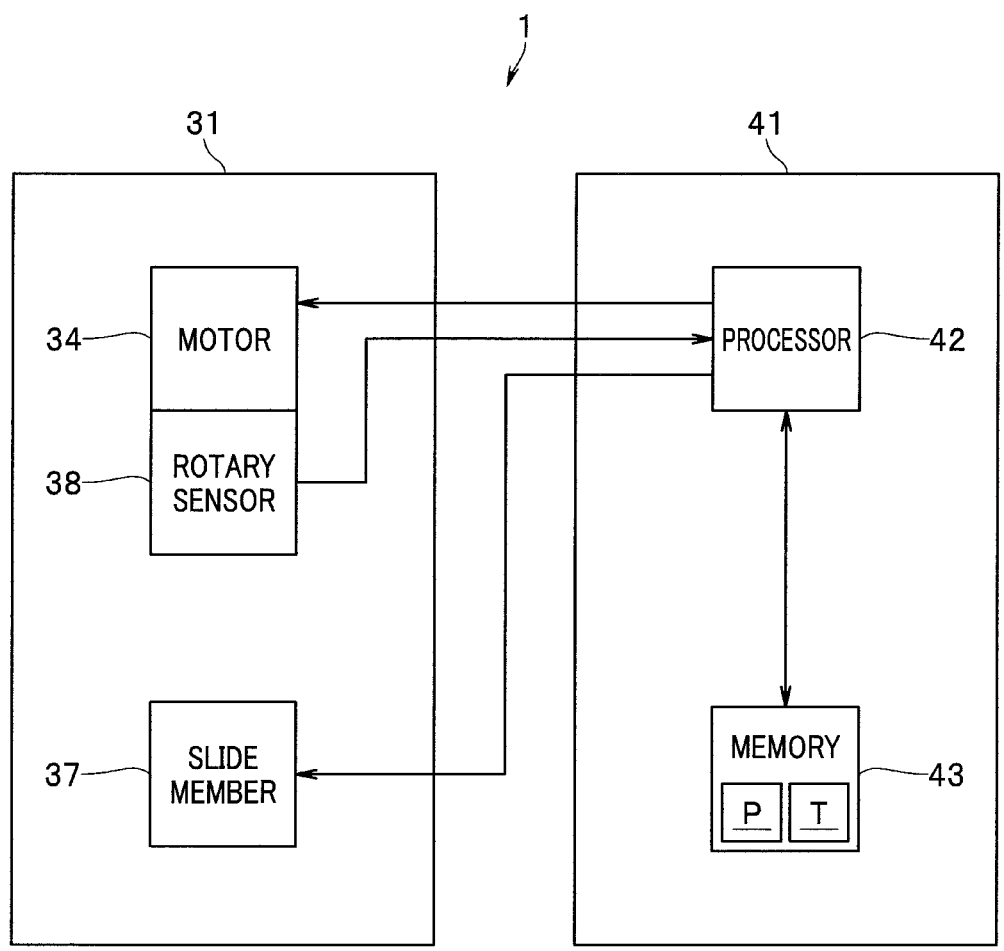
FIG. 2 is a block diagram showing one example of an internal configuration of the optical fiber bundle manufacturing apparatus according to the embodiment of the present invention.

FIG. 1 is a view showing one example of a configuration of an optical fiber bundle manufacturing apparatus 1 according to an embodiment of the present invention. FIG. 2 is a block diagram showing one example of an internal configuration of the optical fiber bundle manufacturing apparatus 1.

As shown in FIG. 1, the optical fiber bundle manufacturing apparatus 1 includes a melting device 11, a coating device 21, a winding device 31 and a controller 41.

The melting device 11 is a wire drawing furnace, for example. The melting device 11 includes a base material charging inlet 12 and a wire drawing opening 13. The melting device 11 melts a base material Bm charged from the base material charging inlet 12 by heating with a heater disposed in the melting device 11. The molten base material Bm is drawn into a wire from the wire drawing opening 13, is naturally cooled, and is formed into optical fiber wire Lw having a predetermined diameter. The base material Bm drawn into a wire may be cooled by a cooling device.

The coating device 21 is a die, for example. The coating device 21 is disposed in front of the optical fiber wire Lw drawn into the wire in an advancing direction. The coating device 21 is formed in a cylindrical shape, and has one end opening 22 and the other end opening 23. The one end opening 22 and the other end opening 23 communicate with each other through an inner peripheral portion of the coating device 21. The coating device 21 includes a coating material supply port 24 through which a coating material is supplied to the inner peripheral portion. The optical fiber wire Lw inserted into the one end opening 22 is covered by the coating material supplied to the inner peripheral portion, and is pulled out from the other end opening 23. The coating material may be cured by a photocuring device or the like after the optical fiber wire is covered by the coating material.

The winding device 31 is disposed in front of the optical fiber wire Lw in an advancing direction and winds up the optical fiber wire Lw drawn from the coating device 21. The winding device 31 includes a winding member 32, support members 33, a motor 34, a restriction member 35, a guide member 36, a slide member 37 and a rotary sensor 38.

The winding member 32 has a drum shape, for example, and includes an outer peripheral surface 32a around which the optical fiber wire Lw is wound, and a rotary shaft 32b which is disposed at the center of rotation of the winding member 32. Cutting grooves 32c and 32d for cutting the wound optical fiber wire Lw by a cutter or the like are formed on the outer peripheral surface 32a in an extending manner in a direction along the rotary axis 22a.

The winding member 32 has a length which allows setting of winding positions X of the optical fiber wire Lw. For example, in an example shown in FIG. 5, the winding positions X have winding positions A to E. In indicating all or some of the winding positions A to E, such winding positions are referred to as the winding positions X. The respective winding positions X are disposed in a spaced-apart manner at a predetermined interval such that the optical fiber wire Lw wound at one winding position X does not overlap with the optical fiber wire Lw wound at other winding positions.

The support members 33 are disposed so as to sandwich both end portions of the winding member 32 between the support members 33, and rotatably and pivotally support both end portions of the rotary shaft 32b. The support members 33 may be configured to be installed on an installation surface such as a floor.

The motor 34 is connected to the rotary shaft 32b, and under control of the controller 41, a rotational force in a winding direction is given to the rotary shaft 32b so that the winding member 32 is rotated.

The restriction member 35 and the guide member 36 are formed using, for example, a fluororesin as a material such that the restriction member 35 and the guide member 36 exhibit a low dynamic friction coefficient with the optical fiber wire Lw. The restriction member 35 and the guide member 36 are disposed between the coating device 21 and the winding member 32. The restriction member 35 and the guide member 36 each include a pair of rod-like members which are disposed in a facing manner in a direction parallel to the rotary axis 22a. The restriction member 35 and the guide member 36 guide the optical fiber wire Lw by the rod-like members.

The restriction member 35 is continuously connected to the other end portion of the coating device 21, and restricts a movement of the optical fiber wire Lw such that the optical fiber wire Lw is not brought into contact with an inner edge of the other end portion.

The guide member 36 is continuously mounted on the slide member 37.

The slide member 37 is disposed between the coating device 21 and the winding member 32. The slide member 37 makes the guide member 36 slide such that the optical fiber wire Lw can be guided to any one of the winding positions X instructed by the controller 41. The slide member 37 includes a rail 37a and a slider 37b.

The rail 37a is disposed outside the winding member 32 in a radial direction, and is disposed parallel to the rotary shaft 32b. The rail 37a may be fixed to the support members 33.

The slider 37b is slidably mounted on the rail 37a, and supports the guide member 36. The slider 37b slides on the rail 37a at a predetermined speed under a control of the controller 41.

The rotary sensor 38 detects a circumferential direction position Y of the winding member 32, and outputs a detection signal to the controller 41 (see FIG. 2). The rotary sensor 38 may be formed of, for example, a magnetic sensor continuously mounted on the support member 33. When the winding member 32 rotates and a magnet mounted on the winding member 32 at a predetermined position approaches the magnetic sensor, the magnetic sensor detects a magnetism of the magnet, and outputs a detection signal to the controller 41.

As shown in FIG. 2, the controller 41 includes a processor 42 and a memory 43. Functions of the processor 42 are realized by executing programs stored in the memory 43.

The processor 42 is connected to the motor 34 and the slide member 37, and controls the motor 34 and the slide member 37. The processor 42 detects the circumferential direction position Y of the winding member 32 depending on a detection signal inputted from the rotary sensor 38.

The memory 43 also stores a winding control program P and a winding position table T besides a program which controls the respective units of the optical fiber bundle manufacturing apparatus 1.

The winding control program P is a program which controls a rotation of the winding member 32 and a movement of the slider 37b toward the winding position X depending on the circumferential direction position Y and the number or rotations Z of the winding member 32.

More specifically, the winding control program P repeats one set of winding control processing until a predetermined number of sets of winding control processing is completed. The predetermined number of sets is determined in advance depending on a kind of the optical fiber bundle Lb.

In one set of winding control processing, the winding control program P controls the winding member 32 and the slider 37b, and makes the winding member 32 wind up the optical fiber wire Lw such that the optical fiber wire Lw is disposed on each of paths between the respective winding positions C, D and E in a branching portion N and the respective winding positions A and B in a branching portion M one time. The branching portion N is a first branching portion. The branching portion M is a second branching portion.

The winding control program P moves the guide member 36 and makes the winding member 32 wind up the optical fiber wire Lw such that the branching portion N, a converging portion V, the branching portion M and a connecting portion W are formed in this order by the optical fiber wire Lw.

In the branching portion N, the optical fiber wire Lw is wound around the winding member 32 at three winding positions C, D and E which are first winding positions.

In the converging portion V, the optical fiber wire Lw is wound around the winding member 32 at the winding position D which is a converging winding position.

In the branching portion M, the optical fiber wire Lw is wound around the winding member 32 at two winding positions A and B which are second winding positions.

In the connecting portion W, the optical fiber wire Lw is wound around the winding member 32 such that the branching portion M is connected to the branching portion N.

For example, when the winding member 32 rotates 6 times in one set and the predetermined number of sets is 100, the winding member 32 rotates 600 times in total. In the branching portion N, at each of three winding positions C, D and E, the optical fiber wire Lw is wound 200 times. In the branching portion M, at each of two winding positions A and B, the optical fiber wire Lw is wound 300 times.

The winding position table T is a table which indicates the winding position X of the optical fiber wire Lw depending on the circumferential direction position Y and the number of rotations Z. The winding position table T is stored in the memory 43 in advance depending on a kind of the optical fiber bundle Lb to be manufactured. To indicate all or some of the numbers of rotations Z1 to Z6, such a number of rotations is referred to as the number of rotations Z. To indicate all or some of the circumferential direction positions Y0 to Y10, such a circumferential direction position is referred to as circumferential direction position Y.

(Manner of Operation)

The manner of operation of the optical fiber bundle manufacturing apparatus 1 of the embodiment is described.

Figure 3:
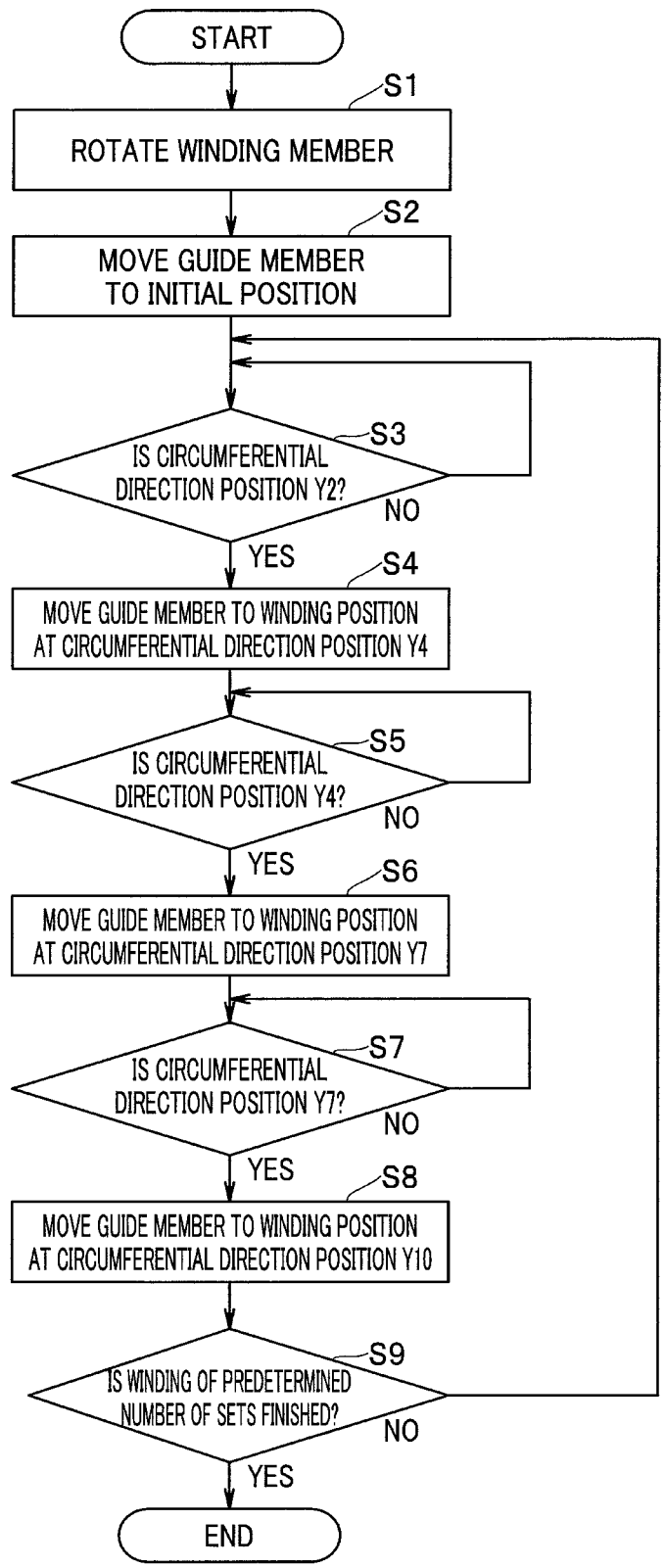
FIG. 3 is a flowchart showing one example of a flow of winding control processing of a controller of the optical fiber bundle manufacturing apparatus according to the embodiment of the present invention.
Figure 4:
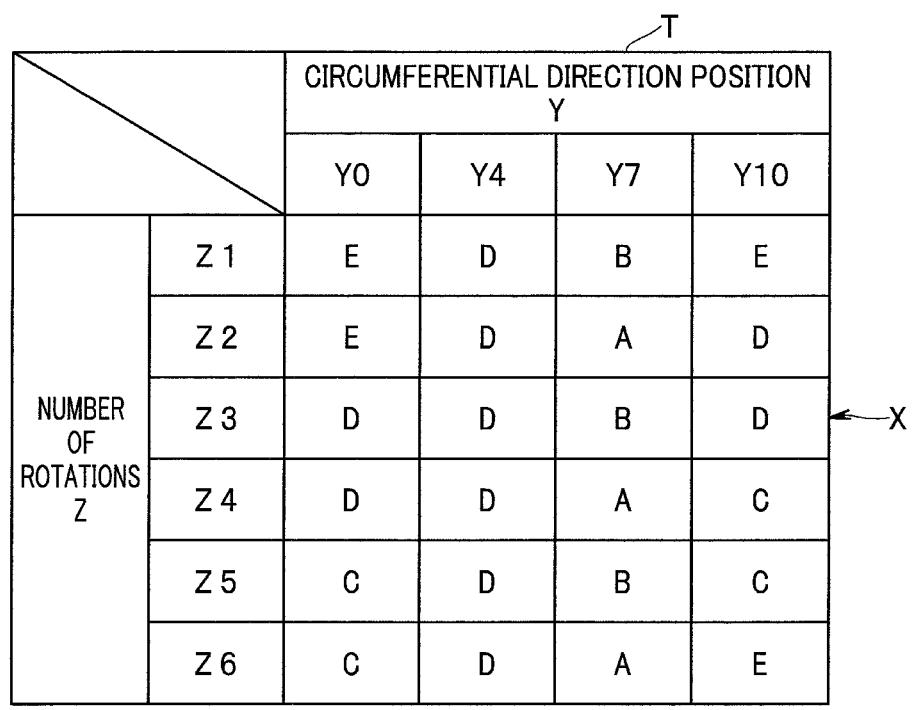
FIG. 4 is a view showing one example of a winding position table of the controller of the optical fiber bundle manufacturing apparatus according to the embodiment of the present invention.

FIG. 3 is a flowchart showing one example of a flow of winding control processing of the controller 41 of the optical fiber bundle manufacturing apparatus 1. FIG. 4 is a view showing one example of the winding position table T.

A user heats the melting device 11 to a predetermined temperature, and charges a coating material into the coating material charging inlet of the coating device 21. When the user charges abase material Bm into the melting device 11, the base material Bm is melted and is drawn so as to form an optical fiber wire Lw. The optical fiber wire Lw passes through the coating device 21 so that the optical fiber wire Lw is covered by a coating material, and the optical fiber wire Lw passes through the restriction member 35 and the guide member 36, and is wound around the winding member 32.

The controller 41 reads the winding control program P and the winding position table T shown in FIG. 4 from the memory 43, and performs winding control processing.

The winding positions X on the winding member 32 are indicated as the winding positions C, A, D, B and E in this order on the outer peripheral surface 32a in a direction along the rotary axis 22a.

The circumferential direction positions Y on the winding member 32 are indicated by the circumferential direction positions Y0 to Y10 in this order on the outer peripheral surface 32a in a circumferential direction.

The numbers of rotations Z1 to Z6 respectively indicate the first-time rotation to sixth-time rotation.

The winding member 32 is rotated (S1). The processor 42 outputs a control signal so that the motor 34 is rotated and the winding member 32 is rotated in the winding direction at a predetermined rotational speed. When the winding member 32 rotates, the optical fiber wire Lw is wound around the winding member 32.

The processor 42 moves guide member 36 to an initial position (S2). The processor 42 reads the initial position from the winding position table T. The processor 42 outputs a control signal so as to move the slide member 37 to the initial position. For example, in the winding position table T shown in FIG. 4, the initial position is the winding position E which is correlated with the number of rotations Z1 and the circumferential direction position Y0.

The processor 42 repeats steps S3 to S9 until the predetermined number of sets of winding is finished. In the first-time winding in the repeated windings, processing with the number of rotations Z1 is performed. Then, sequentially, the winding is repeatedly performed such that processing with the numbers of rotations Z2 to Z6 is performed. Processing performed with the numbers of rotations Z1 to Z6 forms one set. When the processing performed with the number of rotations Z6 is finished, the processing returns to the processing with the number of rotations Z1, and the next set of processing is performed.

The processor 42 determines whether or not the circumferential direction position Y2 is detected (S3). The processor 42 acquires a detection signal from the rotary sensor 38, and detects the circumferential direction position Y of the winding member 32 based on the detection signal. The processor 42 repeats step S3 until the circumferential direction position Y2 is detected (S3: NO). When the circumferential direction position Y2 is detected, the processing advances to step S4 (S3: YES).

The processor 42 moves the guide member 36 to the winding position X at the circumferential direction position Y4 (S4). The processor 42 reads the winding position X at the circumferential direction position Y4 from the winding position table T, and moves the guide member 36 to the winding position X read by the processor 42. In the example shown in FIG. 4, the processor 42 reads the winding position D at the circumferential direction position Y4 with the number of rotations Z1, and moves the guide member 36 to the winding position D.

The processor 42 determines whether or not the circumferential direction position Y4 is detected (S5). The processor 42 repeats step S5 until the circumferential direction position Y4 is detected (S5: NO). When the circumferential direction position Y4 is detected, the processing advances to step S6 (S5: YES).

The processor 42 moves the guide member 36 to the winding position X at the circumferential direction position Y7 (S6). The processor 42 reads the winding position X at the circumferential direction position Y7 from the winding position table T, and moves the guide member 36 to the read winding position X. In the example shown in FIG. 4, the processor 42 moves the guide member 36 to the winding position B at the circumferential direction position Y7 with the number of rotations Z1.

The processor 42 determines whether or not the circumferential direction position Y7 is detected (S7). The processor 42 repeats step S7 until the circumferential direction position Y7 is detected (S7: NO). When the circumferential direction position Y7 is detected, the processing advances to step S8 (S7: YES).

The processor 42 moves the guide member 36 to the winding position X at the circumferential direction position Y10 (S8). The processor 42 reads the winding position X at the circumferential direction position Y10 from the winding position table T, and moves the guide member 36 to the read winding position X read by the processor 42. In the example shown in FIG. 4, the processor 42 moves the guide member 36 to the winding position E at the circumferential direction position Y10 with the number of rotations Z1.

The processor 42 determines whether or not winding of the predetermined number of sets is finished (S9). Processing in steps S3 to S9 is repeated until winding of the predetermined number of sets is finished (S9: NO). When the winding of the predetermined number of sets is finished (S9: YES), the winding control processing is finished.

Figure 5:
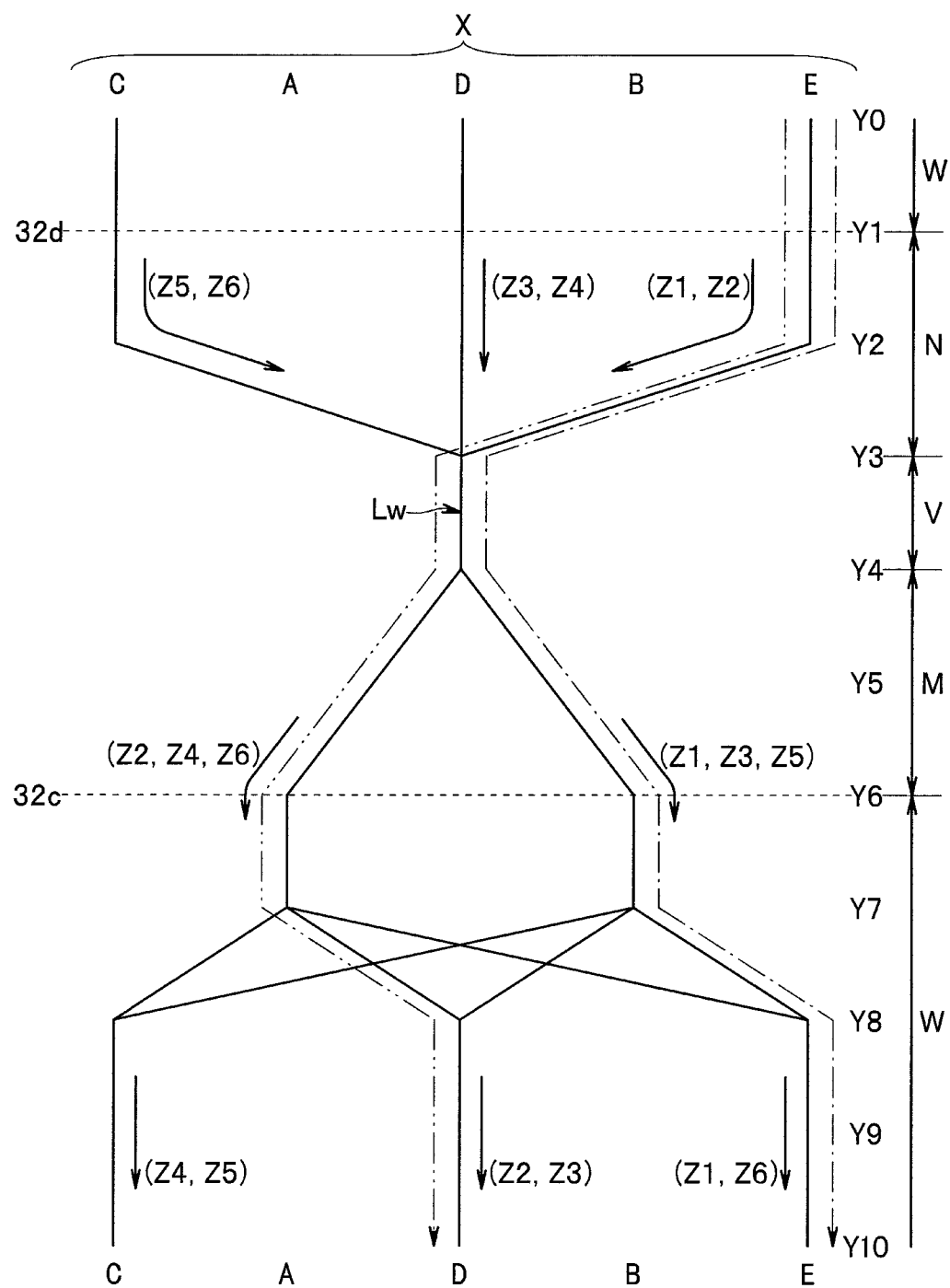
FIG. 5 is an explanatory diagram for describing one example of winding paths of an optical fiber wire in the optical fiber bundle manufacturing apparatus according to the embodiment of the present invention.

FIG. 5 is an explanatory diagram for describing one example of winding paths of the optical fiber wire Lw.

When processing in steps S3 to S9 is repeated by one set with the numbers of rotations Z1 to Z6, the optical fiber wire Lw is wound around the winding member 32 along winding paths shown in FIG. 5. For example, with the number of rotations Z1, the optical fiber wire Lw is wound around the winding member 32 along a winding path indicated by a chain line shown in FIG. 5. With the number of rotations Z2, the optical fiber wire Lw is wound around the winding member 32 along a winding path indicated by a double-dashed chain line. Then, the optical fiber wire Lw is wound around the winding member 32 along a winding path with the numbers of rotations Z3 to Z6 in parenthesis shown in FIG. 5.

Portions of the optical fiber wire Lw at the circumferential direction positions Y1 to Y3 are wound around the winding member 32 at three winding positions C, D and E to form the branching portion N.

Portions of the optical fiber wire Lw at the circumferential direction positions Y3 and Y4 are converged into one winding position D to form the converging portion V.

Portions of the optical fiber wire Lw at the circumferential direction positions Y4 to Y6 are wound around the winding member 32 at two winding positions A and B to form the branching portion M.

Portions of the optical fiber wire Lw at the circumferential direction positions Y0 and Y1 and the circumferential direction positions Y6 to Y10 form the connecting portion W which connects the branching portion M and the branching portion N to each other.

When the optical fiber wire Lw wound around the winding member 32 is cut along the cutting grooves 32c and 32d, the optical fiber bundle Lb is formed. Out of the optical fiber wire Lw wound around the winding member 32, the connecting portion W is discarded.

Figure 6:
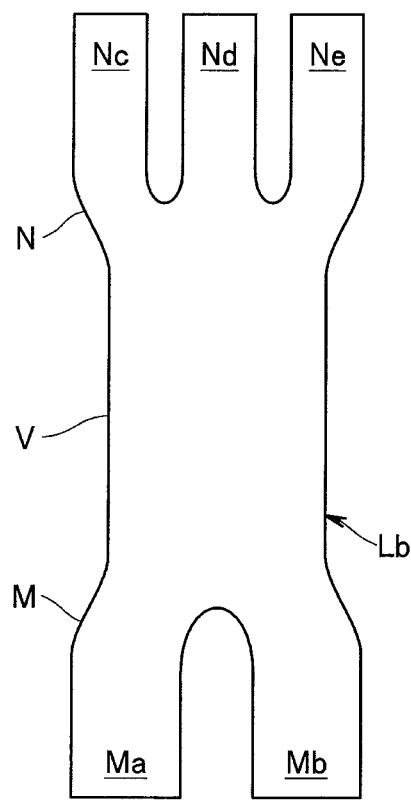
FIG. 6 is a view showing one example of an external appearance configuration of an optical fiber bundle manufactured by the optical fiber bundle manufacturing apparatus according to the embodiment of the present invention.
Figure 7:
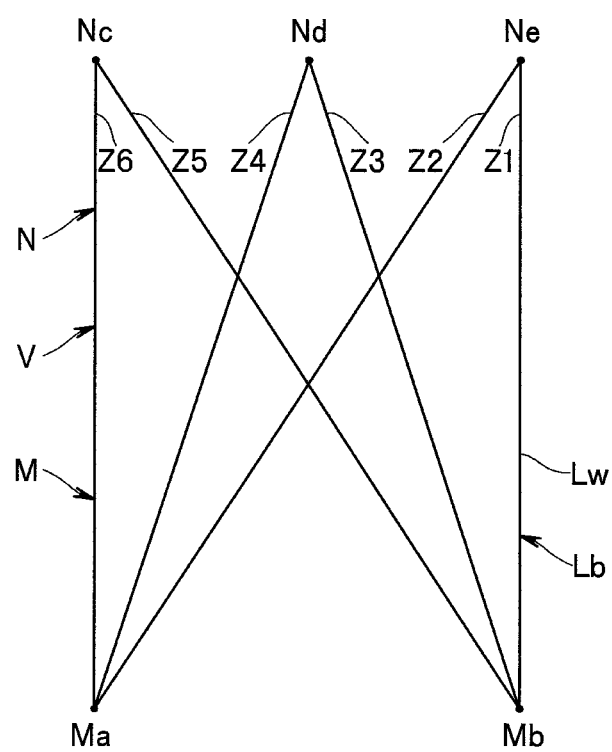
FIG. 7 is an explanatory diagram for describing one example of the configuration of the optical fiber bundle manufactured by the optical fiber bundle manufacturing apparatus according to the embodiment of the present invention.

FIG. 6 is a view showing one example of an external appearance configuration of an optical fiber bundle Lb manufactured by the optical fiber bundle manufacturing apparatus 1. FIG. 7 is an explanatory diagram for describing the configuration of an optical fiber bundle Lb manufactured by the optical fiber bundle manufacturing apparatus 1.

As shown in FIG. 6, in the optical fiber bundle Lb, three branched end portions Nc, Nd and Ne are formed on the branching portion N, and two branched end portions Ma and Mb are formed on the branching portion M. The branched end portions Nc, Nd, Ne, Ma and Mb are respectively formed at the winding positions C, D, E, A and B sequentially.

For example, the optical fiber wire Lw has a diameter of 0.1 mm or less, and the converging portion V is formed of 100 or more portions of the optical fiber wire Lw. However, the embodiment is not limited to such a configuration. In a case of the optical fiber bundle Lb which guides a light such as a laser having a small bright spot, the converging portion V may be formed of 10 or more portions of the optical fiber wire Lw.

As shown in FIG. 7, an optical fiber bundle Lb is formed such that optical fiber wires Lw, the number of which is equal to the predetermined number of sets, are disposed on each of paths between the branched end portion Ne and the branched end portion Mb (the number of rotations Z1), between the branched end portion Ne and the branched end portion Ma (the number of rotations Z2), between the branched end portion Nd and the branched end portion Mb (the number of rotations Z3), between the branched end portion Nd and the branched end portion Ma (the number of rotations Z4), between the branched end portion Nc and the branched end portion Mb (the number of rotations Z5), and between the branched end portion Nc and the branched end portion Ma (the number of rotations Z6).

In other words, in the optical fiber bundle Lb, the number of optical fiber wires Lw is approximately equal between the path between the branched end portion Ne and the branched end portion Mb and the path between the branched end portion Ne and the branched end portion Ma, between the path between the branched end portion Nd and the branched end portion Mb and the path between the branched end portion Nd and the branched end portion Ma, and between the path between the branched end portion Nc and the branched end portion Mb and the path between the branched end portion Nc and the branched end portion Ma.

Accordingly, the optical fiber bundle Lb, a light guide Lg formed of the optical fiber bundle Lb, and an endoscope 111 including the light guide Lg can more uniformly guide a light to each of the paths between the respective branched end portions Nc, Nd and Ne and respective branched end portions Ma and Mb.

The optical fiber bundle manufacturing apparatus 1 can manufacture the optical fiber bundle Lb by winding up the optical fiber wire Lw drawn from the melting device 11 by the winding member 32 and hence, the optical fiber bundle Lb can be manufactured efficiently.

(Configuration of Endoscope 111 Having Light Guide Lg)

Subsequently, the configuration of the endoscope 111 having the light guide Lg is described.

The light guide Lg has an optical fiber bundle Lb.

Figure 8:
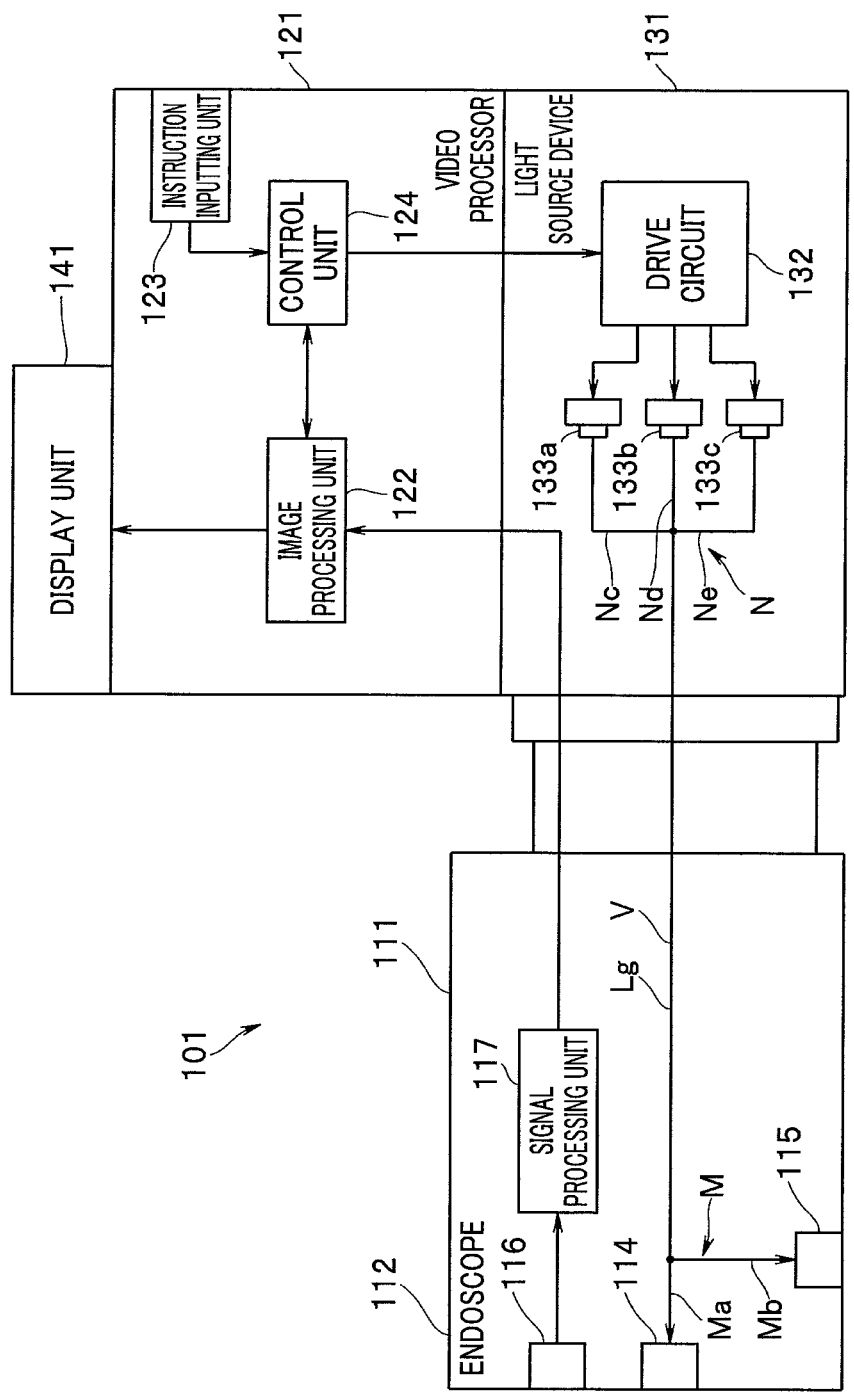
FIG. 8 is a block diagram showing one example of an endoscope having a light guide formed of the optical fiber bundle manufactured by the optical fiber bundle manufacturing apparatus according to the embodiment of the present invention.

FIG. 8 is a block diagram showing one example of the endoscope 111 having the light guide Lg formed of the optical fiber bundle Lb manufactured by the optical fiber bundle manufacturing apparatus 1.

As shown in FIG. 8, an endoscope apparatus 101 includes the endoscope 111, a video processor 121, a light source device 131 and a display unit 141.

As shown in FIG. 8, the endoscope 111 is detachably connected to the light source device 131.

The endoscope 111 includes an insertion section 112 having an elongated shape to be inserted into an object. Illumination light emitting units 114 and 115 and an image pickup unit 116 are mounted on a distal end member 113 disposed on a distal end portion of the insertion section 112.

The illumination light emitting units 114 and 115 radiate illumination light guided by the light guide Lg to the object. The branched end portions Ma and Mb of the light guide Lg are respectively connected to the illumination light emitting units 114 and 115. The illumination light emitting unit 114 radiates illumination light to an area in front of the distal end member 113, for example. The illumination light emitting unit 115 radiates illumination light to an area on a side of the distal end member 113, for example.

The image pickup unit 116 includes an image pickup element formed of a CCD, a CMOS or the like. The image pickup unit 116 is connected with a signal processing unit 117. The image pickup unit 116 converts a light returned from the object into an image pickup signal, and outputs the image pickup signal to the signal processing unit 117.

The signal processing unit 117 is a circuit which performs processing of an image pickup signal. The signal processing unit 117 is connected to the video processor 121 via the light source device 131. The signal processing unit 117 applies correlated double sampling processing to an image pickup signal inputted from the image pickup unit 116 to convert the image pickup signal into a digital signal, and outputs the digital signal to the video processor 121. The signal processing unit 117 may be configured to control an AGC gain, a frame rate and a shutter speed of the image pickup unit 116 in response to an instruction inputted by a user.

The video processor 121 includes an image processing unit 122, an instruction inputting unit 123 and a control unit 124.

The image processing unit 122 is a circuit which applies a predetermined image processing to an image pickup signal inputted from the signal processing unit 117, and outputs a display image on the display unit 141 under a control of the control unit 124. The predetermined image processing includes, for example, gamma correction processing, white balance processing, contour emphasis processing, zooming in and out processing, and matrix processing. The predetermined image processing may include all or some of these processings, or may include processing other than these processings.

The instruction inputting unit 123 includes operation instruments such as operation buttons, and various instructions can be inputted by a user. When an instruction is inputted by the user, the instruction inputting unit 123 outputs a control signal to the control unit 124 depending on the inputted instruction.

The control unit 124 is a circuit which performs controls of respective units in the endoscope 111. The control unit 124 detects an image pickup signal inputted to the image processing unit 122, outputs a control signal to the light source device 131, and controls brightness of illumination light of the light source device 131 depending on brightness of the image pickup signal.

The light source device 131 includes a drive circuit 132 and light sources 133a, 133b and 133c.

The drive circuit 132 outputs a drive current depending on a control signal inputted from the control unit 124, and controls the light sources 133a, 133b and 133c.

The branched end portion Nc is connected to the light source 133a, the branched end portion Nd is connected to the light source 133b, and the branched end portion Ne is connected to the light source 133c. The light sources 133a, 133b and 133c differ from each other in a wavelength of an outputted illumination light such as red, green, blue. The light sources 133a, 133b and 133c output illumination lights depending on drive currents inputted from the drive circuit 132.

The display unit 141 includes an LCD, an OLED or the like, and displays a display image inputted from the image processing unit 122.

In other words, the endoscope 111 includes the light guide Lg which is manufactured by the optical fiber bundle manufacturing apparatus 1. Both a distal end side and a proximal end side of the light guide Lg are branched in plurality, and the light guide Lg guides illumination lights from the plurality of light sources 133a, 133b and 133c to the plurality of illumination light emitting units 114 and 115 mounted on the distal end member 113 of the insertion section 112.

The light guide Lg is mounted on the endoscope 111 which is to be inserted into the object. In the light guide Lg, three kinds of illumination lights are incident on the branching portion N from the light sources 133a, 133b and 133c, and the illumination lights are radiated from two illumination light emitting units 114 and 115 toward the object via the branching portion M.

According to the embodiment, the light guide Lg and the endoscope 111 which includes the light guide Lg can more uniformly radiate lights incident from light incident side end portions branched in plurality from the light emitting side end portions branched in plurality.

The optical fiber bundle manufacturing apparatus 1 and the method of manufacturing an optical fiber bundle can more efficiently manufacture the light guide Lg. Further, by mounting the light guide Lg which is efficiently manufactured by the optical fiber bundle manufacturing apparatus 1 and the method of manufacturing an optical fiber bundle on the endoscope 111, it is possible to relatively easily provide the endoscope 111 which can more uniformly guide lights between the respective branched end portions on one side and the respective branched end portions on the other side.

Modification 1 of Embodiment

In the embodiment, winding control processing is performed along the winding paths set in accordance with the winding position table T. However, the winding paths are not limited to such paths. With respect to the winding paths, winding control processing may be performed along winding paths set in accordance with a winding position table T1.

Figure 9:
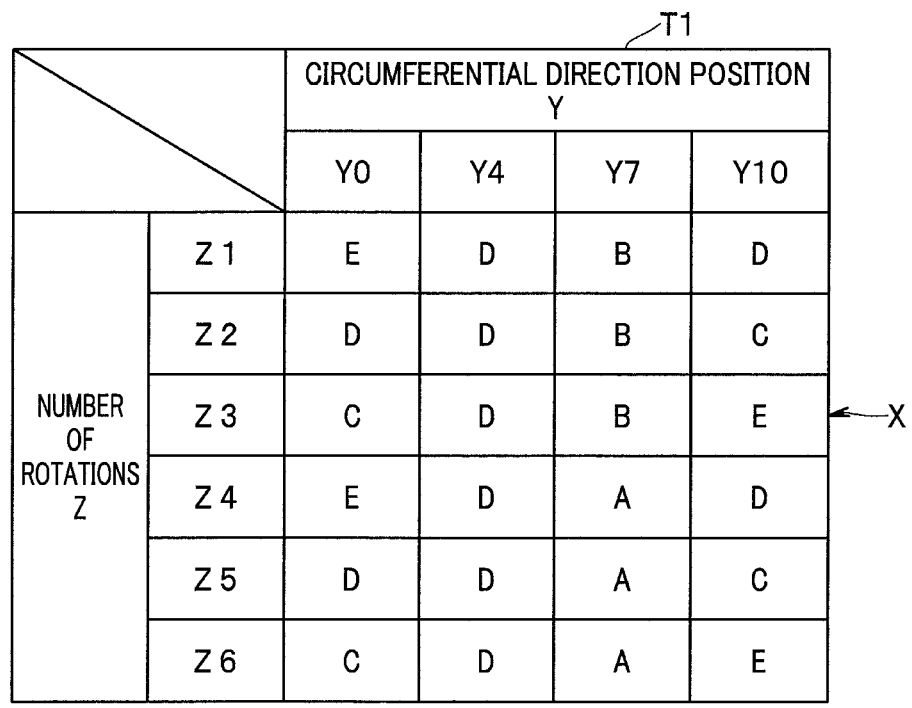
FIG. 9 is a view showing one example of a winding position table of a controller of an optical fiber bundle manufacturing apparatus according to a modification 1 of the embodiment of the present invention.

FIG. 9 is a view showing one example of the winding position table T1 of a controller 41 of an optical fiber bundle manufacturing apparatus 1 according to a modification 1 of the embodiment of the present invention. In the modification, the description of an example of the configurations which are identical with the corresponding components of the above-mentioned embodiment is omitted.

In the modification 1, an optical fiber bundle Lb is manufactured by performing winding control processing in accordance with the winding position table T1 shown in FIG. 9. In the optical fiber bundle Lb, optical fiber wires Lw, the number of which is equal to the predetermined number of sets, are disposed on each of paths between a branched end portion Ne and a branched end portion Mb (the number of rotations Z1), between a branched end portion Nd and the branched end portion Mb (the number of rotations Z2), between a branched end portion Nc and the branched end portion Mb (the number of rotations Z3), between the branched end portion Ne and a branched end portion Ma (the number of rotations Z4), between the branched end portion Nd and the branched end portion Ma (the number of rotations Z5), and between the branched end portion Nc and the branched end portion Ma (the number of rotations Z6).

Modification 2 of Embodiment

In the embodiment and the modification 1, the branching portion N is branched into three pieces, and the branching portion M is branched into two pieces. However, the number of branches is not limited to such numbers. For example, both the branching portion N and the branching portion M may each be branched into three pieces.

Figure 10:
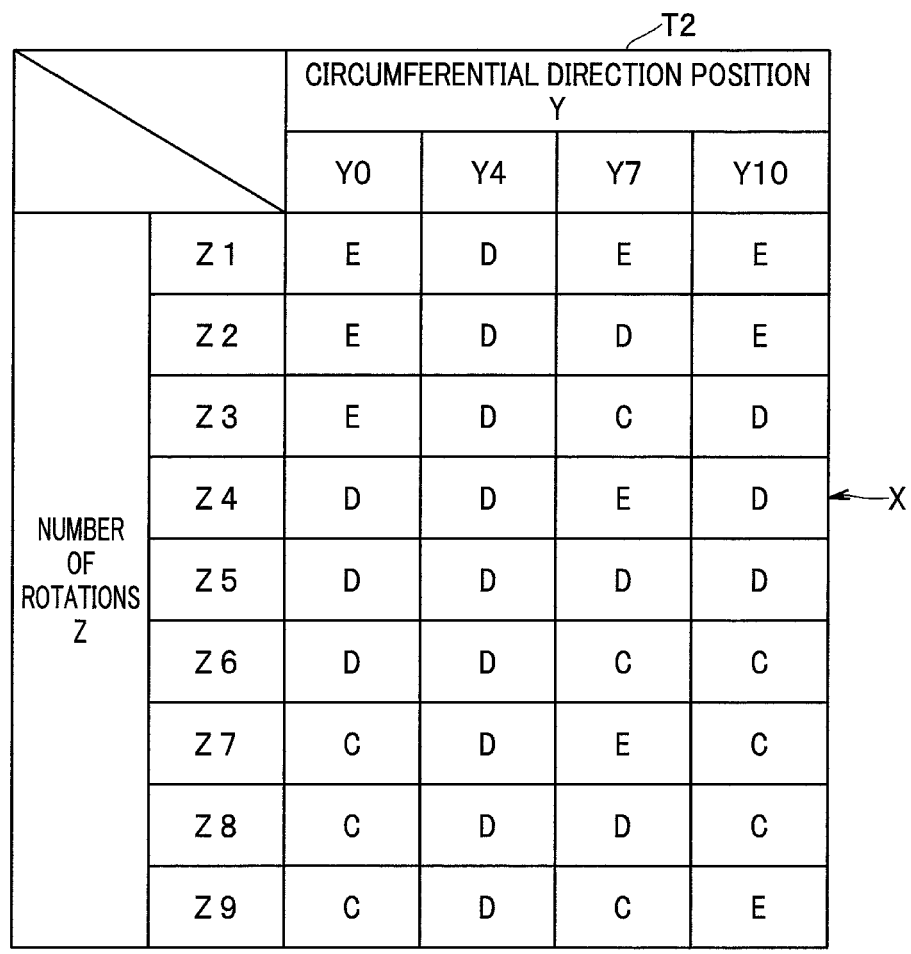
FIG. 10 is a view showing one example of a winding position table of a controller of an optical fiber bundle manufacturing apparatus according to a modification 2 of the embodiment of the present invention.
Figure 11:
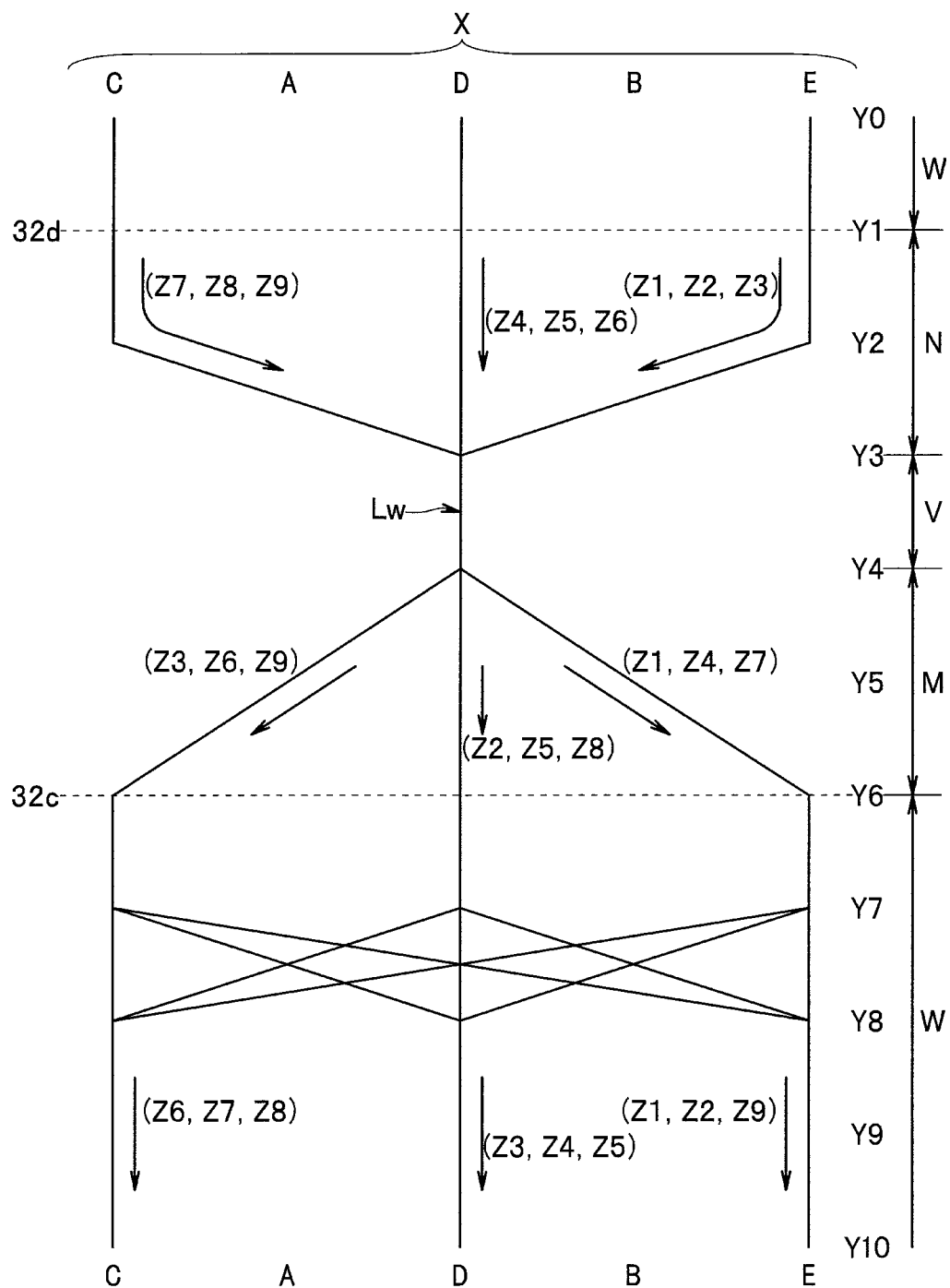
FIG. 11 is an explanatory view for describing one example of winding paths of an optical fiber wire of the optical fiber bundle manufacturing apparatus according to the modification 2 of the embodiment of the present invention.
Figure 12:
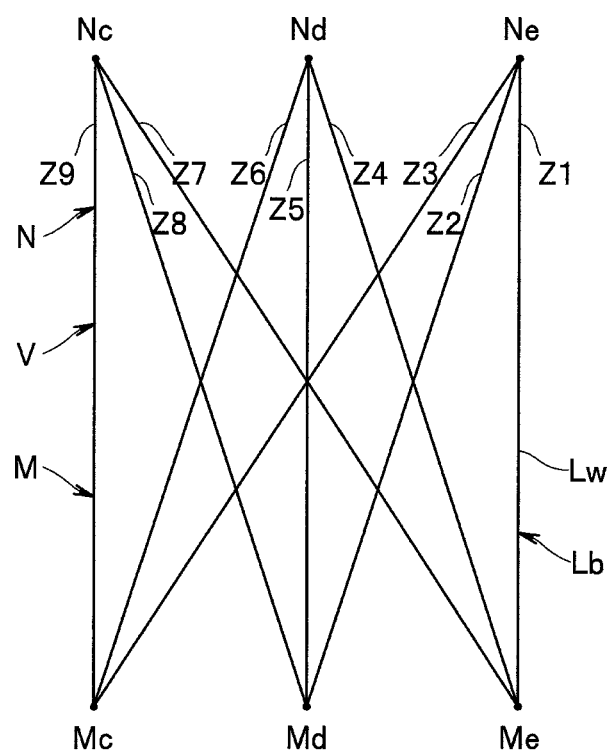
FIG. 12 is an explanatory diagram for describing one example of a configuration of an optical fiber bundle manufactured by the optical fiber bundle manufacturing apparatus according to the modification 2 of the embodiment of the present invention.

FIG. 10 is a view showing one example of a winding position table T2 of a controller 41 of an optical fiber bundle manufacturing apparatus 1 according to a modification 2 of the embodiment of the present invention. FIG. 11 is an explanatory view for describing one example of winding paths of an optical fiber wire Lw. FIG. 12 is an explanatory diagram for describing one example of a configuration of an optical fiber bundle Lb. In the modification, the description of one example of the configurations which are identical with the components of the above-mentioned embodiment and the modification 1 is omitted. In the modification 2, the number of rotations Z indicates all or a part of the numbers of rotations Z1 to Z9.

In the modification, when winding control processing is performed in accordance with the winding position table T2 shown in FIG. 10, an optical fiber wire Lw is wound around a winding member 32 along winding paths shown in FIG. 11. By cutting the optical fiber wire Lw at cutting grooves 32c and 32d after winding control processing is finished, the optical fiber bundle Lb is formed.

As shown in FIG. 12, in the optical fiber bundle Lb, the optical fiber wires Lw, the number of which is equal to the predetermined number of sets, are disposed on each of paths between a branched end portion Ne and a branched end portion Me (the number of rotations Z1), between the branched end portion Ne and a branched end portion Md (the number of rotations Z2), between the branched end portion Ne and a branched end portion Mc (the number of rotations Z3), between a branched end portion Nd and the branched end portion Me (the number of rotations Z4), between the branched end portion Nd and the branched end portion Md (the number of rotations Z5), between the branched end portion Nd and the branched end portion Mc (the number of rotations Z6), between a branched end portion Nc and the branched end portion Me (the number of rotations Z7), between the branched end portion Nc and the branched end portion Md (the number of rotations Z8), and between the branched end portion Nc and the branched end portion Mc (the number of rotations Z9).

Modification 3 of Embodiment

In the modification 2, the branching portion N and the branching portion M are respectively branched into three pieces. However, the number of branches is not limited to such a number. For example, the branching portion N may be branched into four pieces, and the branching portion M may be branched into three pieces.

Figure 14:
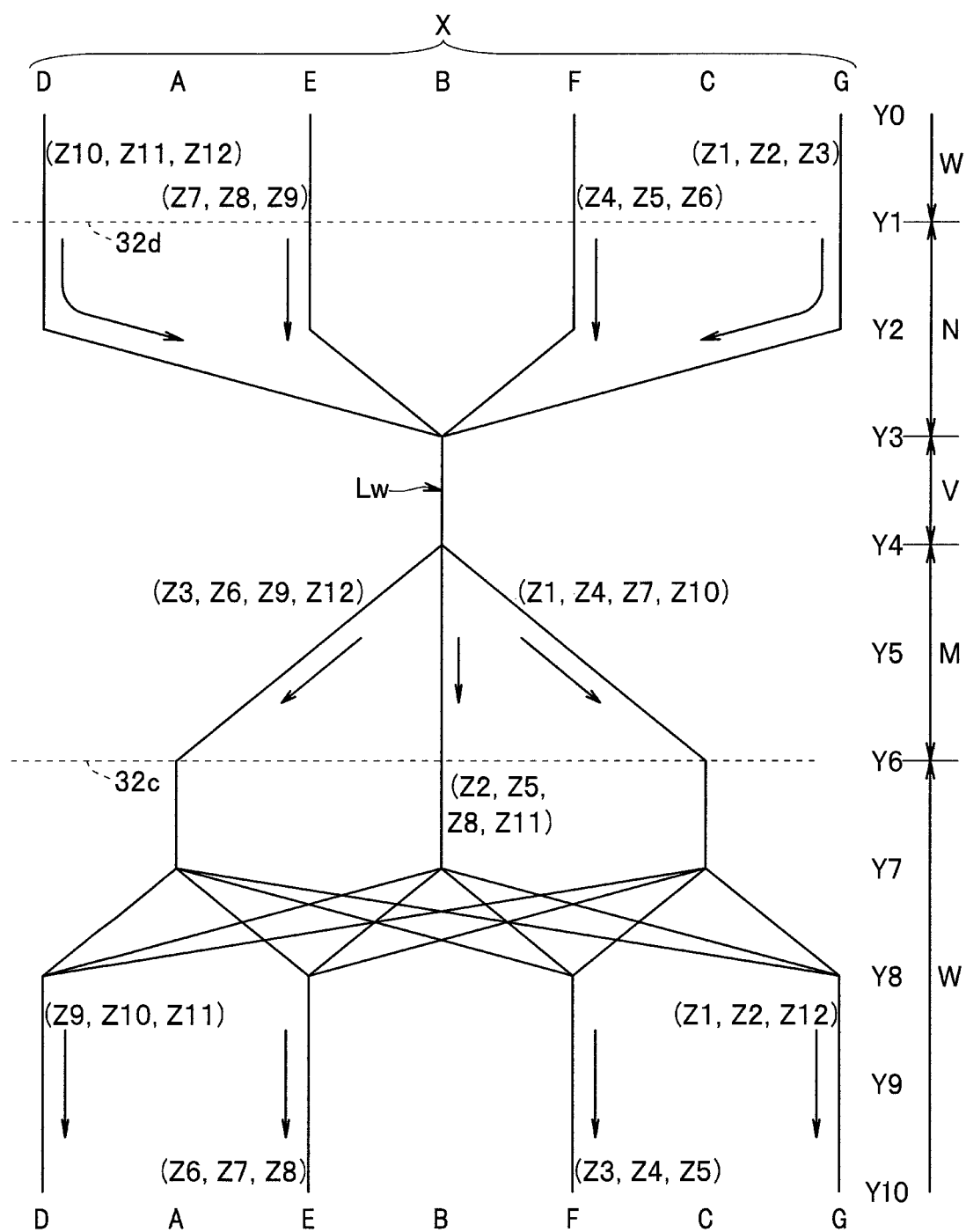
FIG. 14 is an explanatory diagram for describing one example of winding paths of an optical fiber wire of the optical fiber bundle manufacturing apparatus according to the modification 3 of the embodiment of the present invention.
Figure 15:
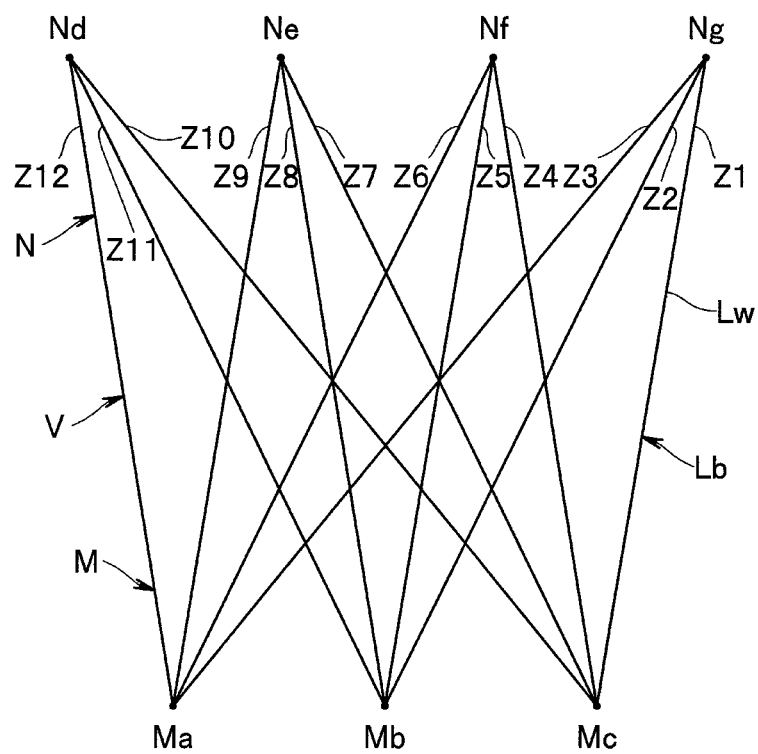
FIG. 15 is an explanatory diagram for describing one example of a configuration of an optical fiber bundle manufactured by the optical fiber bundle manufacturing apparatus according to the modification 3 of the embodiment of the present invention.

FIG. 13 is a view showing one example of a winding position table T3 of a controller 41 of an optical fiber bundle manufacturing apparatus 1 according to a modification 3 of the embodiment of the present invention. FIG. 14 is an explanatory diagram for describing one example of winding paths of an optical fiber wire Lw. FIG. 15 is an explanatory diagram for describing one example of a configuration of an optical fiber bundle Lb. In the modification 3, the description of one example of the configurations which are identical with the components of the above-mentioned embodiment and other modifications is omitted. In the modification 3, a winding position X indicates all or a part of winding positions A to G. Further, in the modification 3, the number of rotations Z indicates all or a part of the numbers of rotations Z1 to Z12.

In the modification 3, when winding control processing is performed in accordance with the winding position table T3 shown in FIG. 13, an optical fiber wire Lw is wound around a winding member 32 along winding paths shown in FIG. 14. By cutting the optical fiber wires Lw at cutting grooves 32c and 32d after winding control processing is finished, the optical fiber bundle Lb is formed.

As shown in FIG. 15, in the optical fiber bundle Lb, optical fiber wires Lw, the number of which is equal to the predetermined number of sets, are disposed on each of paths between a branched end portion Ng and a branched end portion Mc (the number of rotations Z1), between the branched end portion Ng and a branched end portion Mb (the number of rotations Z2), between the branched end portion Ng and a branched end portion Ma (the number of rotations Z3), between a branched end portion Nf and the branched end portion Mc (the number of rotations Z4), between the branched end portion Nf and the branched end portion Mb (the number of rotations Z5), between the branched end portion Nf and the branched end portion Ma (the number of rotations Z6), between a branched end portion Ne and the branched end portion Mc (the number of rotations Z7), between the branched end portion Ne and the branched end portion Mb (the number of rotations Z8), between the branched end portion Ne and the branched end portion Ma (the number of rotations Z9), between a branched end portion Nd and the branched end portion Mc (the number of rotations Z10), between the branched end portion Nd and the branched end portion Mb (the number of rotations Z11), and between the branched end portion Nd and the branched end portion Ma (the number of rotations Z12).

Modification 4 of Embodiment

In the modification 3, the branching portion N is branched into four pieces, and the branching portion M is branched into three pieces. However, the number of branches is not limited to such numbers. For example, the branching portion N may be branched into five pieces, and the branching portion M may be branched into two pieces.

Figure 17:
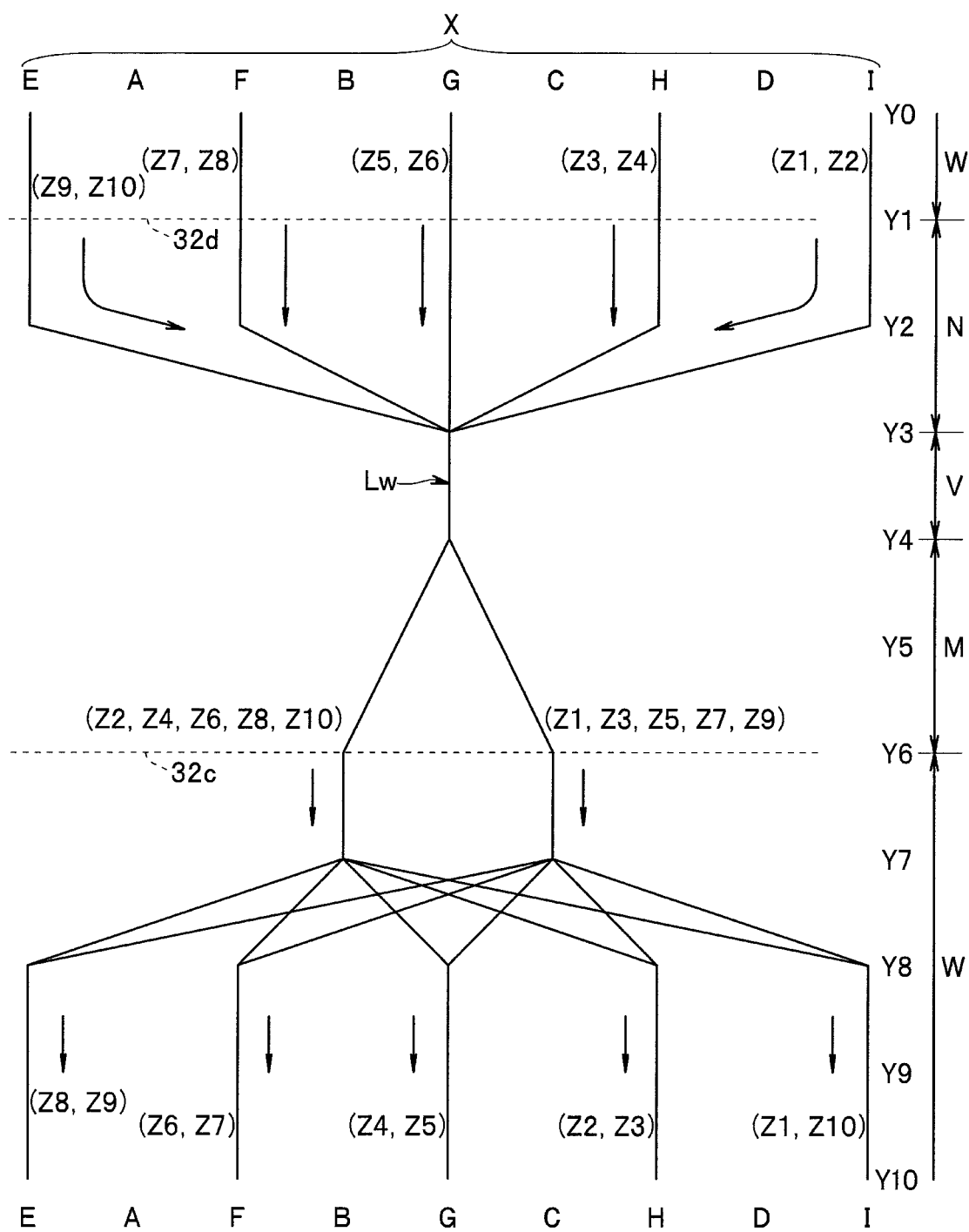
FIG. 17 is an explanatory diagram for describing one example of winding paths of an optical fiber wire of the optical fiber bundle manufacturing apparatus according to the modification 4 of the embodiment of the present invention.
Figure 18:
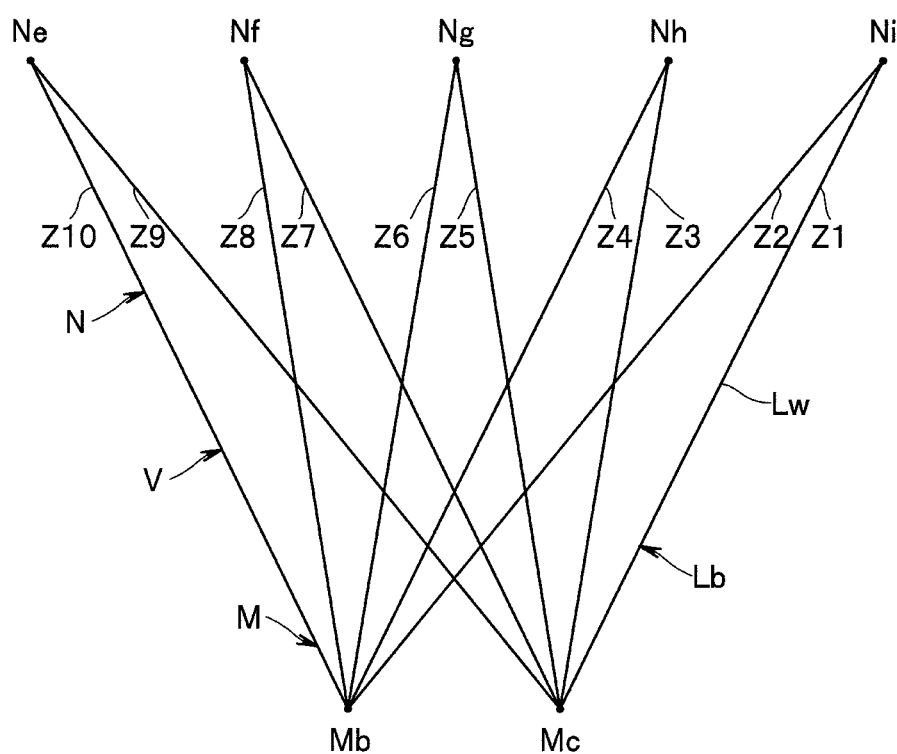
FIG. 18 is an explanatory diagram for describing one example of a configuration of an optical fiber bundle manufactured by the optical fiber bundle manufacturing apparatus according to the modification 4 of the embodiment of the present invention.

FIG. 16 is a view showing one example of a winding position table T4 of a controller 41 of an optical fiber bundle manufacturing apparatus 1 according to a modification 4 of the embodiment of the present invention. FIG. 17 is an explanatory diagram for describing one example of winding paths of an optical fiber wire Lw. FIG. 18 is an explanatory diagram for describing one example of a configuration of an optical fiber bundle Lb. The modification 4 omits the description of one example of the configurations which are identical with the components of the above-mentioned embodiment and other modifications. In the modification 4, a winding position X indicates all or a part of winding positions A to I. Further, in the modification 4, the number of rotations Z indicates all or a part of the numbers of rotations Z1 to Z10.

In the modification 4, when winding control processing is performed in accordance with the winding position table T4 shown in FIG. 16, an optical fiber wire Lw is wound around a winding member 32 along winding paths shown in FIG. 15. By cutting the optical fiber wire Lw at cutting grooves 32c and 32d after winding control processing is finished, the optical fiber bundle Lb is formed.

As shown in FIG. 16, in the optical fiber bundle Lb, the optical fiber wires Lw, the number of which is equal to the predetermined number of sets, are disposed on each of paths between a branched end portion Ni and a branched end portion Mc (the number of rotations Z1), between the branched end portion Ni and a branched end portion Mb (the number of rotations Z2), between a branched end portion Nh and the branched end portion Mc (the number of rotations Z3), between the branched end portion Nh and the branched end portion Mb (the number of rotations Z4), between a branched end portion Ng and the branched end portion Mc (the number of rotations Z5), between the branched end portion Ng and the branched end portion Mb (the number of rotations Z6), between a branched end portion Nf and the branched end portion Mc (the number of rotations Z7), between the branched end portion Nf and the branched end portion Mb (the number of rotations Z8), between a branched end portion Ne and the branched end portion Mc (the number of rotations Z9), and between branched end portion Ne and the branched end portion Mb (the number of rotations Z10).

Modification 5 of Embodiment

In the embodiment and the modifications, in the optical fiber bundle manufacturing apparatus 1, the movement of the guide member 36 is controlled depending on the winding position tables T, T1, T2, T3 and T4. However, the optical fiber bundle manufacturing apparatus 1 may be configured such that a guide member 36 is disposed at any one of winding positions X at random.

When the predetermined number of sets is set to a larger value, in accordance with the Law of Large numbers, optical fiber wires Lw are approximately uniformly disposed between respective first branched end portions and respective second branched end portions.

In other words, in the modification 5, a processor 42 controls the guide member 36 such that the optical fiber wires Lw are approximately uniformly disposed between the respective first branched end portions and the respective second branched end portions. The processor 42 also controls the guide member 36 such that the optical fiber wire Lw is disposed at random in a converging portion V.

In the embodiment and the modifications, the variations of the number of branches in the branching portion N and in the branching portion M have been described. However, the numbers of respective branching in the branching portion N and in the branching portion M are not limited to such numbers. The numbers of respective branching at the branching portion N and at the branching portion M may be different from the corresponding numbers of branching described in the embodiment and the modifications.

The plurality of variations may be stored in the memory 43, and the processor 42 may read any one of variations from the memory 43 in response to an instruction from a user, and may control the guide member 36. For example, the memory 43 may store a first winding path where the number of branches of the first branching portion and the number of branches of the second branching portion are equal to each other, and a second winding path where the number of branches of the first branching portion and the number of branches of the second branching portion differ from each other, and the processor 42 may read either one of the first winding path and the second winding path from the memory 43 and may control the guide member 36.

In other words, the optical fiber bundle manufacturing apparatus 1 includes a winding member 32, the guide member 36, and the processor 42. The winding member 32 rotates about a rotary shaft 32b in a winding direction, and winds up the optical fiber wires Lw. The guide member 36 moves in a direction parallel to a rotary shaft 32b, and guides the optical fiber wire Lw to any one of p (p being a natural number of 2 or more) first winding positions, a converging winding position and q (q being a natural number of 2 or more) second winding positions on the winding member 32. The processor 42 moves the guide member 36 such that the first branching portion which is branched into p branches at the first winding positions, the converging portion V which converges the first branching portion at the converging winding position, the second branching portion which is branched into q branches from the converging portion at the second winding positions, and the connecting portion W where the first branching portion and the second branching portion are connected to each other are formed in this order on the winding member 32 by the optical fiber wire Lw.

The processor 42 moves the guide member 36 such that the arrangement number of portions of the optical fiber wire Lw on each of paths between the respective first branched end portions and the respective second branched end portions is arbitrarily set in a distributed manner. For example, substantially the same number of optical fiber wires Lw are distributed to the respective first branched end portions and the respective second branched end portions. The processor 42 may move the guide member 36 during the rotation of the winding member 32.

A method of manufacturing the optical fiber bundle Lb prepares: the winding member 32 which winds up the optical fiber wire Lw by rotating in the winding direction about the rotary shaft 32b; and the guide member 36 which moves in the direction parallel to the rotary shaft 32b, and guides the optical fiber wire Lw to the winding positions X on the winding member 32. Then, winding controlling processing is performed where the winding member 32 is rotated, and the optical fiber wire Lw is wound up while moving the guide member 36 such that the arrangement number of portions of the optical fiber wire Lw on each of paths between p (p being a natural number of 2 or more) first winding positions on the winding member 32 and q (q being a natural number of 2 or more) second winding positions on the winding member 32 which differ from the first winding positions in the circumferential direction position Y is arbitrarily set in a distributed manner. For example, the arrangement numbers of the portions of the optical fiber wire Lw on the paths between p first winding positions and q (q being a natural number of 2 or more) second winding positions are set substantially equal.

Cutting grooves 32c and 32d form a cutting device. The cutting grooves 32c and 32d cut the optical fiber wire Lw wound around the winding member 32 at the first branching portion and the second branching portion. The cutting device may include a cutting tool which cuts the optical fiber wire Lw under a control of the processor 42.

In the embodiment, unless the respective steps of each processing are not contrary to the natures of these respective steps, the order of performing the steps may be changed, a plurality of steps may be performed simultaneously, or the steps may be performed in a different order in each processing. Further, all or a part of the respective steps in respective processing of the embodiment may be realized by a hardware.

As described above, the present invention is applicable to a case where an arrangement number distribution control is made so as to set the arrangement numbers of the portions of the optical fiber wire Lw on the paths between the respective first branched end portions and the respective second branched end portions different from each other instead of setting the arrangement numbers of the portions optical fiber wire Lw on the paths between the respective first branched end portions and the respective second branched end portions substantially equal.

The present invention is not limited to the above-mentioned embodiment, and various modifications, improvements and the like are conceivable without departing from the gist of the present invention.

What is claimed is:

1. An optical fiber bundle manufacturing apparatus comprising:
 a winding member configured to rotate about a rotary axis to wind up an optical fiber wire;

a guide member configured to move in a direction parallel to the rotary axis to guide the optical fiber wire to any one of:
  p first winding positions,
  a converging winding position, and
  q second winding positions,
on an outer peripheral surface of the winding member, where p is a natural number of 2 or more and q is a natural number of 2 or more, and where p is a different number than q; and
  a processor configured to perform processing to move the guide member such that
    a first branching portion branching into p branches at the first winding positions,
    a converging portion converging the first branching portion branching into p branches into one at the converging winding position,
    a second branching portion branching into q branches from the converging portion converging into one at the second winding positions, and
    a connecting portion connecting the first branching portion and the second branching portion,
are formed in this order by the optical fiber wire.

2. The optical fiber bundle manufacturing apparatus according to claim 1,
  wherein the processor is configured to perform the processing to move the guide member during rotation of the winding member.

3. The optical fiber bundle manufacturing apparatus according to claim 1, further comprising a memory,
  wherein the memory is configured to store a first winding path where a number of branches of the first branching portion and a number of branches of the second branching portion are equal to each other, and a second winding path where the number of branches of the first branching portion and the number of branches of the second branching portion differ from each other, and
  wherein the processor is configured to read either one of the first winding path and the second winding path from the memory, and to perform the processing to move the guide member according the first winding path and the second winding path read from the memory.

4. The optical fiber bundle manufacturing apparatus according to claim 1,
  wherein the first branching portion includes p first branched end portions,
  wherein the second branching portion includes q second branched end portions, and
  wherein the processor is configured to perform the processing to move the guide member such that the optical fiber wire is approximately uniformly disposed between the respective first branched end portions and respective second branched end portions.

5. The optical fiber bundle manufacturing apparatus according to claim 4, wherein the processor is configured to perform the processing to move the guide member such that the optical fiber wire is disposed at random in the converging portion.

6. The optical fiber bundle manufacturing apparatus according to claim 1, further comprising a cutting device configured to cut the optical fiber wire wound around the winding member at the first branching portion and the second branching portion.

7. The optical fiber bundle manufacturing apparatus according to claim 1,
  wherein the optical fiber wire has a diameter of 0.1 mm or less, and
  wherein the processor is configured to perform the processing to move the guide member such that the converging portion is formed of 10 or more portions of the optical fiber wire.

8. The optical fiber bundle manufacturing apparatus according to claim 1,
  wherein the first branching portion includes p first branched end portions,
  wherein the second branching portion includes q second branched end portions, and
  wherein the processor is configured to perform the processing to move the guide member such that an arrangement number of portions of the optical fiber wire on each of paths between the respective first branched end portions and the respective second branched end portions is arbitrarily set in a distributed manner.

9. The optical fiber bundle manufacturing apparatus according to claim 8, wherein the processor is configured to perform the processing to move the guide member such that the arrangement numbers are set substantially equal.

10. The optical fiber bundle manufacturing apparatus according to claim 9, wherein the processor is configured to perform processing to move the guide member such that the connecting portion branches into p branches from q branches.

11. The optical fiber bundle manufacturing apparatus according to claim 1, wherein the connecting portion is different than the converging portion.

12. The optical fiber bundle manufacturing apparatus according to claim 1,
  wherein the processor is configured to perform processing to rotate the winding member a predetermined number of times, where the guide member is moved to form the first branching portion, the converging portion, the second branching portion and the connecting portion in the order in each time of the predetermined number of times of rotation of the winding member, and
  wherein the predetermined number of times is determined based on a kind of the optical fiber bundle being manufactured.

13. The optical fiber bundle manufacturing apparatus according to claim 1,
  wherein the processor is configured to perform processing to move the guide member to any one of:
    one of a predetermined first winding position of the p first winding positions,
    the converging winding position, and
    one of a predetermined second winding position of the q second winding positions, based on which of the first branching portion, the converging portion, the second branching portion and the connection portion is being formed and which rotation of a predetermined number of rotations of the winding member is being performed.

14. The optical fiber bundle manufacturing apparatus according to claim 1,
  wherein the winding member defines a first cutting groove at the first branching portion and a second cutting groove at the second branching portion where the first cutting groove and the second cutting groove are each configured to receive a cut such that portions of the optical fiber wire traversing the first branching portion, the converging portion and the second branching portion form the optical fiber bundle.

15. A method of manufacturing an optical fiber bundle, the method comprising:

rotating a winding member about a rotary axis to wind up an optical fiber wire, and moving a guide member in a direction parallel to the rotary axis to guide the optical fiber wire to any one of:
- p first winding positions,
- a converging winding position, and
- q second winding positions, on an outer peripheral surface of the winding member, where p is a natural number of 2 or more and q is a natural number of 2 or more, and where p is a different number than q, wherein moving the guide member comprises moving the guide member such that:
- a first branching portion branching into p branches at the first winding positions,
- a converging portion converging the first branching portion branching into p branches into one at the converging winding position,
- a second branching portion branching into q branches from the converging portion converging into one at the second winding positions, and
- a connecting portion connecting the first branching portion and the second branching portion, are formed in this order by the optical fiber wire.

16. The method of manufacturing an optical fiber bundle according to claim 15, wherein the moving the guide member is performed while the rotating the winding member such that an arrangement numbers of portions of the optical fiber wire on each of paths between the p first winding positions and the q second winding positions are set substantially equal.

* * * * *